(12) United States Patent
Joseph et al.

(10) Patent No.: US 7,602,883 B2
(45) Date of Patent: Oct. 13, 2009

(54) MULTI-DENSITY SKIN MARKER

(75) Inventors: Karen Joseph, Tarzana, CA (US); Adam Press, Los Angeles, CA (US); Falcon Sutton, Canyon Country, CA (US)

(73) Assignee: St. John Companies, Inc., Valencia, CA (US)

( * ) Notice: Subject to any disclaimer, the term of this patent is extended or adjusted under 35 U.S.C. 154(b) by 0 days.

(21) Appl. No.: 11/781,174

(22) Filed: Jul. 20, 2007

(65) Prior Publication Data

US 2009/0022272 A1  Jan. 22, 2009

(51) Int. Cl.
 *H05G 1/28* (2006.01)
(52) U.S. Cl. .................. 378/162; 378/165
(58) Field of Classification Search ......... 378/162–165, 378/204, 205; 600/414, 426
 See application file for complete search history.

(56) References Cited

U.S. PATENT DOCUMENTS

| | | | |
|---|---|---|---|
| 4,692,325 A | 9/1987 | Kritzler | |
| 4,860,331 A | 8/1989 | Williams et al. | |
| 5,383,233 A | 1/1995 | Russell | |
| 5,394,456 A | 2/1995 | Livingston | |
| 5,394,457 A | 2/1995 | Leibinger et al. | |
| 5,702,128 A | 12/1997 | Maxim et al. | |
| 5,755,746 A | 5/1998 | Lifshey et al. | |
| 5,848,125 A | 12/1998 | Arnett | |
| RE36,461 E | 12/1999 | Russell et al. | |
| 6,041,094 A | 3/2000 | Russell | |
| 6,160,870 A | 12/2000 | Jacobson | |
| 6,269,148 B1 | 7/2001 | Jessop et al. | |
| 6,419,680 B1 | 7/2002 | Cosman et al. | |
| 6,687,533 B1 | 2/2004 | Hirano et al. | |
| 6,985,558 B1 | 1/2006 | Russell | |
| 2003/0100830 A1 | 5/2003 | Zhong et al. | |
| 2004/0116802 A1 | 6/2004 | Jessop et al. | |
| 2005/0157847 A1 | 7/2005 | Marn | |
| 2006/0072706 A1 | 4/2006 | Russell | |

*Primary Examiner*—Jurie Yun
(74) *Attorney, Agent, or Firm*—Christie, Parker & Hale, LLP

(57) ABSTRACT

A multi-density skin marker for medical imaging exams is provided. The skin marker contains a multi-density imaging body. In one embodiment, a multi-density skin marker includes a marker substrate and a multi-density imaging body supported by the marker substrate. The multi-density imaging body comprises a first portion having a first radiographic density and a second portion having a second radiographic density. The two radiographic densities differ, such that a radiographic image of the multi-density skin marker comprises a plurality of shades.

28 Claims, 8 Drawing Sheets

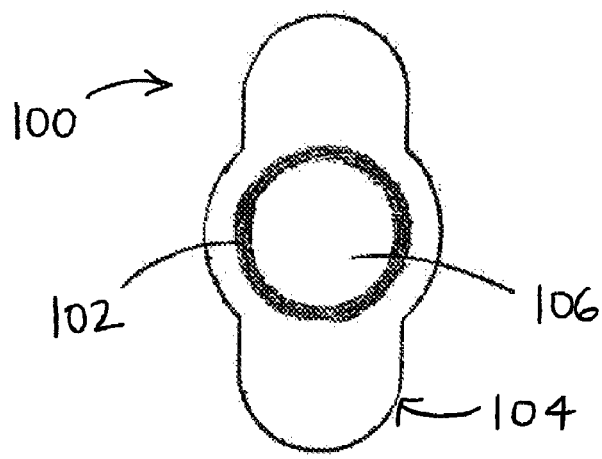
FIG. 1A
Prior Art
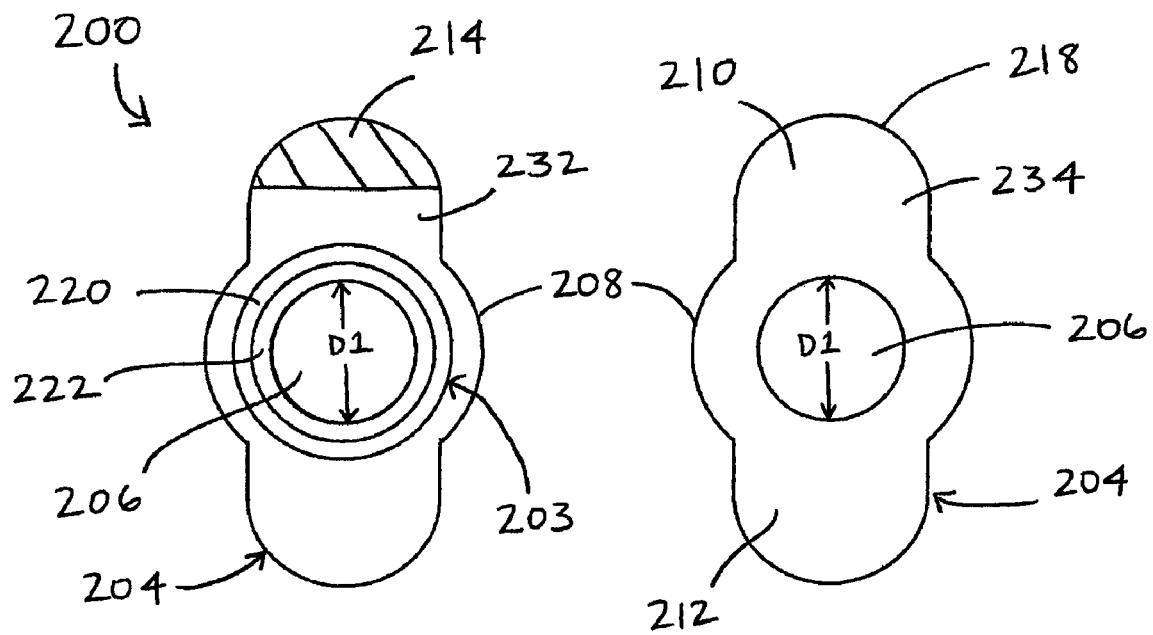
FIG. 2A
FIG. 2B

MULTI-DENSITY SKIN MARKER

FIELD OF THE INVENTION

The present invention relates to skin markers for medical imaging exams, and more particularly to multi-density radiolucent skin markers for medical imaging exams.

BACKGROUND OF THE INVENTION

Radiolucent skin markers are often used in the medical profession to identify particular areas of interest on a patient for a medical imaging exam. A small marker with a radiolucent or semiopaque imaging body can be adhered to the patient's skin next to or near the area of interest, such as a skin protrusion or lesion or a mass below the skin. An example of a prior art skin marker 100 is shown in FIG. 1A. The marker 100 includes a marker substrate 104 with a central opening 106 and an imaging body 102. In FIG. 1A, the imaging body 102 is shaped as a ring that encircles the central opening 106. The marker 100 may be adhered to a patient's skin such that the area of interest is encircled by the imaging ring 102. Other prior art markers include imaging bodies with other shapes, such as a small "BB" or spherical ball. The patient undergoes the medical imaging exam with the marker 100 in place on the patient's skin. The exam may be a computed tomography (CT) scan, x-ray, magnetic resonance imaging (MRI), or other radiographic imaging exam. A common radiographic exam is a mammography, an x-ray imaging exam of breast tissue.

An example of an image of the prior art marker 100 is shown in FIG. 1B. The radiolucent marker appears as a bright ring on the resulting image, so that the radiologist or other medical caregiver can identify the location of the skin protrusion, lesion, mass, or other area of interest that was marked by the marker. The skin marker thus enables the radiologist to make a more accurate diagnosis.

"Radiolucent" and "radiopaque" refer to the radiographic density of the imaging marker. A radiolucent marker allows some radiation to pass through it, while a radiopaque marker reflects radiation and prevents it from passing through the marker. The resulting radiographic image of a radiopaque marker will be denser and will appear brighter than that of a radiolucent marker. Materials with high thicknesses and/or high densities are more radiopaque, and produce a brighter, denser radiographic image, than thinner and/or less dense materials. Thus, the radiographic density of a marker refers to the density of the radiographic image of the marker.

Radiolucent skin markers can fail to register on the radiographic image, especially when the x-ray or other exam is used to image very dense tissue, such as dense breast tissue. Dense tissue requires longer exposure to the radiation in order to obtain a clear image of the tissue. During longer exposure times, the radiation fully penetrates the radiolucent marker, causing it to disappear from the resulting image. Therefore, it is desirable to provide a skin marker that appears more clearly on images of dense tissue.

Radiolucent skin markers can also fail to provide a three-dimensional perspective on the resulting image. A small "BB" or spherical marker appears the same from all directions, so the circle that appears on the x-ray or other image cannot indicate to the radiologist the three-dimensional positioning of the patient. A relatively flat marker with no change in thickness can also fail to add depth to an image. Therefore, it is also desirable to provide a skin marker that adds a three-dimensional perspective to the image.

SUMMARY

The present invention relates to skin markers for medical exams, and more particularly to multi-density radiolucent skin markers for medical imaging exams.

In an exemplary embodiment of the invention, a multi-density skin marker includes a marker substrate and a multi-density imaging body supported by the marker substrate, wherein the multi-density imaging body comprises a first portion having a first radiographic density and a second portion having a second radiographic density. The first radiographic density differs from the second radiographic density such that a radiographic image of the multi-density skin marker comprises a plurality of shades.

In another embodiment of the invention, a multi-density skin marker includes a marker substrate having an adhesive surface; and a multi-density imaging body supported by the marker substrate and comprising a first imaging shape and a second imaging shape adhered to and at least partially overlapping the first imaging shape.

In another embodiment of the invention, a multi-density radiographic image of a multi-density skin marker having a first portion with a first radiographic density and a second portion with a second radiographic density that differs from the first radiographic density includes a first image of the first portion having a first shade and a second image of the second portion having a second shade different from the first shade.

In another embodiment of the invention, a method of using a multi-density skin marker for a radiographic imaging exam includes locating an area of interest on a patient's skin; adhering to the patient's skin near the area of interest a multi-density skin marker having a first portion with a first radiographic density and a second portion with a second radiographic density that differs from the first radiographic density; and obtaining a multi-density radiographic image of the area of interest and the multi-density skin marker.

In another embodiment of the invention, a method of manufacturing a multi-density skin marker includes cutting a first outer perimeter of a first imaging body from a first radiolucent material; cutting a second outer perimeter of a second imaging body from a second radiolucent material; adhering the first and second imaging bodies to each other in an overlapping relationship; and adhering the first and second imaging bodies to a marker substrate.

BRIEF DESCRIPTION OF THE DRAWINGS

These and other features and advantages of the present invention will become appreciated as the same become better understood with reference to the specification, claims and appended drawings wherein:

FIG. 1A is a front view of a prior art skin marker;

FIG. 2A is a rear view of a multi-density skin marker in an embodiment according to the invention;

FIG. 2B is a front view of the multi-density skin marker of FIG. 2A;

Figures 1B, 2D:
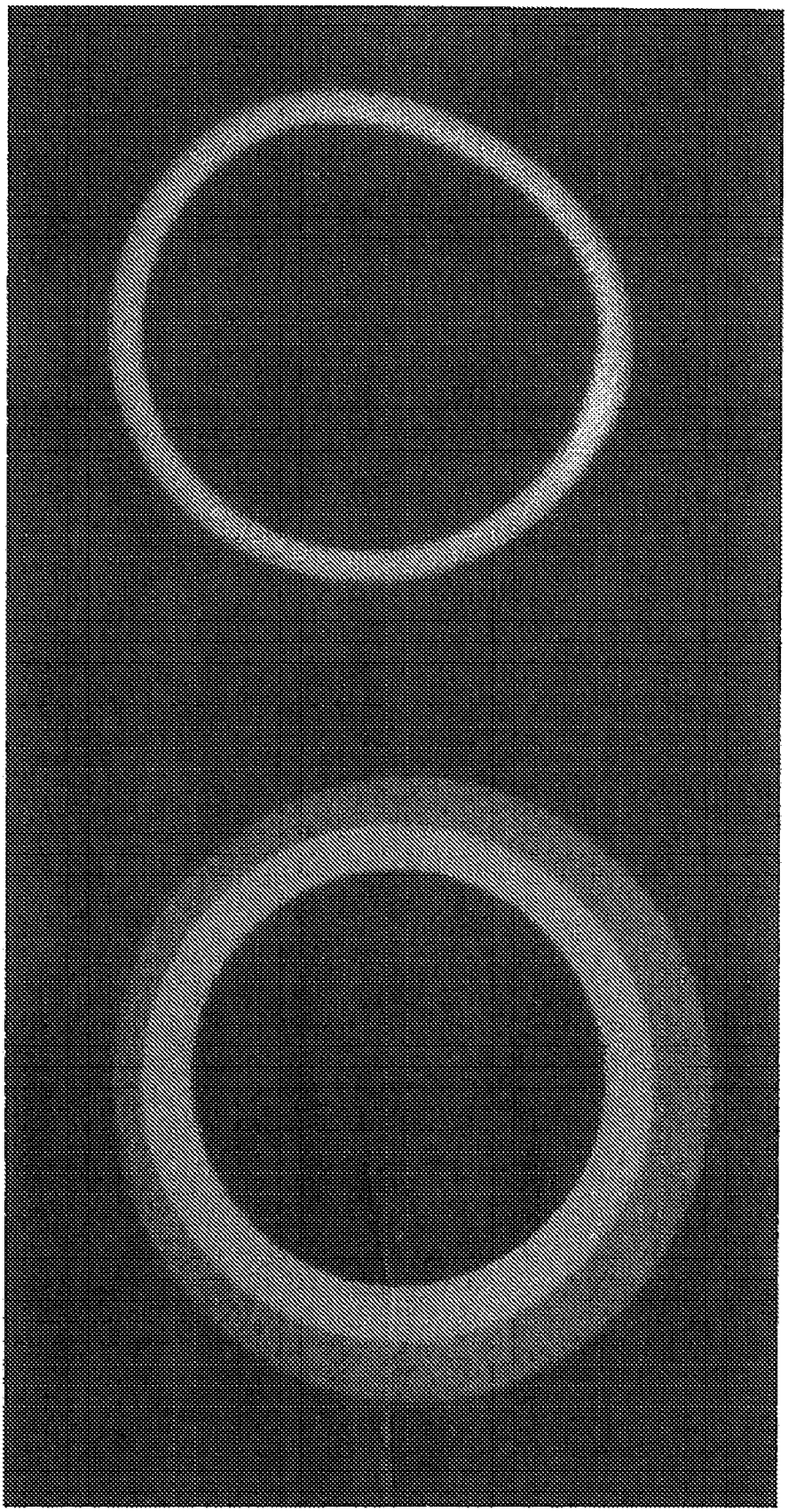
FIG. 1B is a black and white photo reproduction of a radiographic image of a prior art skin marker.
FIG. 2D is a black and white photo reproduction of a radiographic image of a multi-density skin marker in an embodiment according to the invention.

Some dimensions in the figures have been exaggerated for clarity and are not necessarily to scale.

DETAILED DESCRIPTION

The detailed description set forth below in connection with the appended drawings is intended as a description of the presently preferred embodiments of a multi-density skin marker provided in accordance with the present invention and is not intended to represent the only forms in which the present invention may be constructed or utilized. The description sets forth the features of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

The present invention relates to skin markers for medical imaging exams, and more particularly to multi-density skin markers for medical imaging exams. The skin marker contains a multi-density imaging body having two portions with different radiographic densities. In one embodiment, the multi-density imaging body includes two or more imaging bodies or shapes that at least partially overlap with each other. The area of overlap creates an area of higher radiographic density, which appears brighter in the resulting image than the non-overlapping areas of the imaging bodies. The radiographic image of the overlapping area will thus have a different tone or shade than the radiographic image of the non-overlapping area. This multi-density skin marker appears more clearly than prior art markers in images of dense tissue, because the higher density overlapping area is not as quickly washed out during long exposure times. The multi-density marker can also add depth to the image by varying the thickness of the marker where the two or more imaging bodies overlap, thus adding a third dimension to the image.

In other embodiments, the multi-density imaging body includes two or more imaging bodies with different thicknesses, different densities, or both, such that they have different radiographic densities. These imaging bodies may be positioned adjacent to each other, apart from each other, or overlapping each other. In yet another embodiment of the invention, the multi-density imaging body includes a single imaging body having a varying density and/or a varying thickness, such that different portions of the imaging body have different radiographic densities. The term "multi" as used herein includes two or more.

Referring to FIGS. 2A and 2B, a marker 200 according to an exemplary embodiment of the invention includes a marker substrate 204 and a multi-density imaging body 203. Any suitable paper, plastic, cloth, or other label stock may be used for the marker substrate 204. The marker substrate 204 should be suitable for contact with a patient's skin.

The bottom surface 232 of the marker 200 is shown in FIG. 2A, and the top surface 234 is shown in FIG. 2B. The bottom surface 232 of the marker 200 is at least partially covered with a medical grade adhesive approved for skin contact. Any suitable adhesive that is appropriate for direct contact with a patient's skin may be applied to the bottom surface 232 of the marker 200. This bottom surface 232 is placed directly on the patient's skin near, above, or around the area of interest to be identified in the medical imaging exam. The top surface 234 faces away from the patient's skin, and may contain any desired symbols, images, letters, and/or colors to provide information about the marker, the imaging exam, the patient, and/or other relevant information, and/or to improve the aesthetic appearance of the marker 200.

The marker 200 includes a round central portion 208 located between first and second ends 210 and 212 that form extensions or tabs on either side of the central portion 208. Underneath one tab 210, on the bottom surface 232, is a nonadhesive area 214 which does not adhere to the patient's skin. This non-adhesive area 214 provides an easy lift tab for removing the skin marker 200 from the patient's skin after the imaging exam. The non-adhesive area 214 can be formed by leaving a portion of the release liner 640 (shown in FIG. 6) adhered to the area 214, as described more fully below.

The marker 200 also includes a central opening 206 in the middle of the central portion 208. The central opening 206 can be used to expose a skin protrusion, lesion, or other area of interest that the marker 200 is being used to identify. For example, the marker 200 can be placed around a mole such that the mole extends through the central opening 206. However, the central opening 206 is entirely optional, and may be absent in other embodiments. The marker may simply be placed next to or near the skin protrusion, lesion, or area of interest to identify that area, without the use of a central opening.

The marker substrate 204 supports a multi-density imaging body 203. The imaging 15 body 203 shown in FIG. 2a includes two imaging shapes 220 and 222, which in this embodiment are shaped as rings. The imaging rings 220 and 222 encircle the central opening 206. In the embodiment shown, the two rings and the central opening 206 have the same inner diameter D1, which is approximately 0.5 inches. This diameter may vary in other embodiments according to the desired size of the marker 200 and the opening 206.

While the imaging rings 220, 222 are shown in FIG. 2A on the bottom surface 232 of the marker 200, the rings may alternatively be located on the top surface 234 of the marker, facing away from the patient's skin.

Figure 2C:
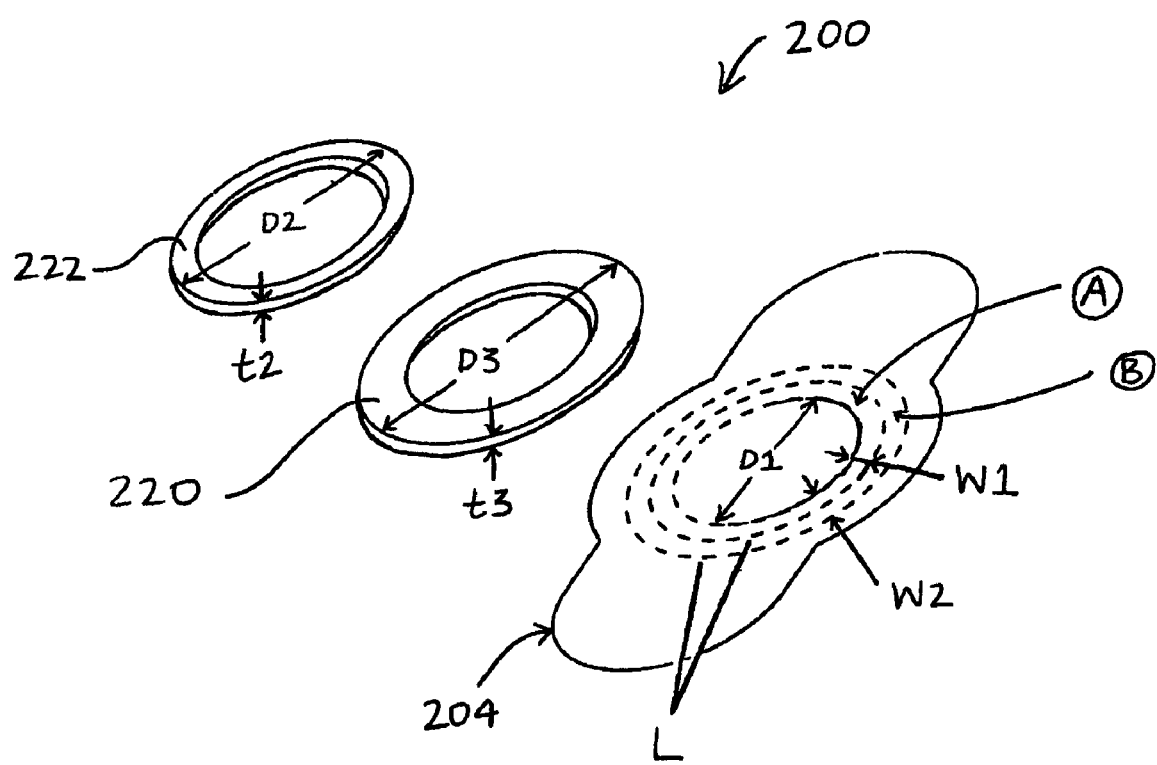
FIG. 2C is an exploded perspective view of the multi-density skin marker of FIG. 2A.
Figures 3A, 3B:
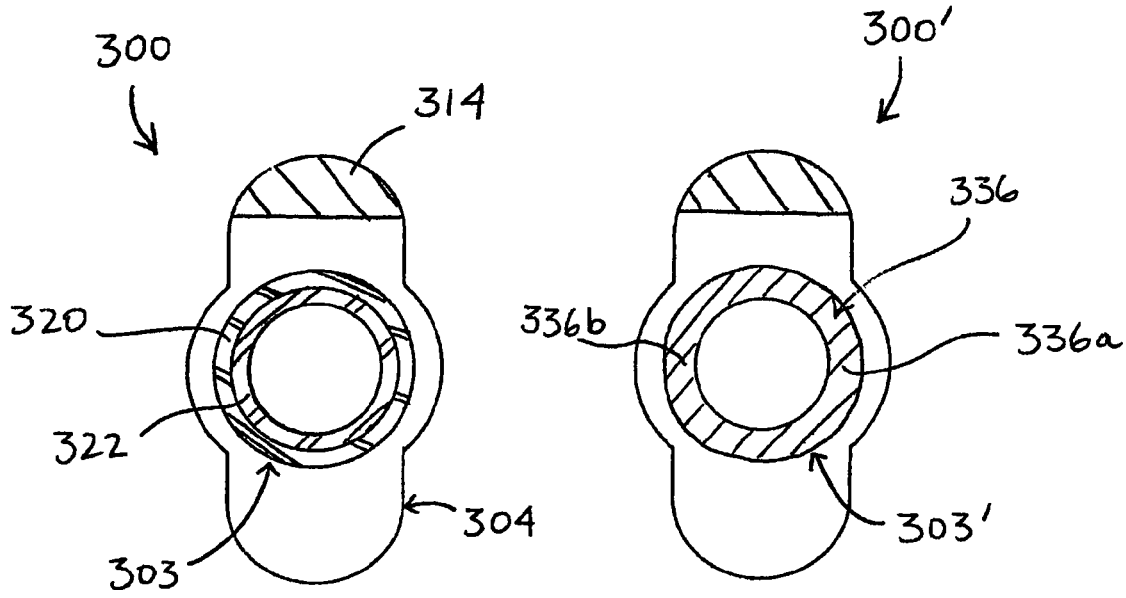
FIG. 3A is a rear view of a multi-density skin marker in an embodiment according to the invention.
FIG. 3B is a rear view of a multi-density skin marker in an embodiment according to the invention.

Referring to FIG. 2C, the outer ring 220 is located between the marker substrate 204 and the inner ring 222. The inner ring 222 has an outside diameter or perimeter D2. The outer ring 220 has an outside diameter or perimeter D3 that is greater than D2. In the embodiment shown, the outside diameter D2 of the inner ring 222 is approximately ⅝ inches, and the outside diameter D3 of the outer ring 220 is approximately ⅞ inches. These diameters may be varied in other embodiments. The ring widths W1 and W2 may also be varied in other embodiments according to the desired amount of overlap of the two rings, the shape of the imaging body 203, the shape of the marker 200, the presence and size of the central opening 206, and other factors.

The dotted lines L in FIG. 2C show where the imaging rings 220, 222 are placed on the marker substrate 204. When the two imaging rings are placed on the marker substrate 204, the inner ring 222 overlaps with the inner portion of the outer ring 220. The overlapping rings create the overlapping area A on the marker substrate 204. The outer portion of the outer ring 220 remains uncovered by the inner ring 222, forming a non-overlapping area B.

In the embodiment shown, each of the two rings has a thickness t2 and t3 of 6 millimeters ("mils"). The overlapping area A has a thickness equal to the combined thickness of the two rings 220, 222—12 mils in the embodiment shown. The non-overlapping area B has a thickness equal to the thickness of the outer ring 220. These thicknesses may be varied in other embodiments. For example, either or both of the rings 220, 222 may have thicknesses ranging anywhere from about 4 to about 12 mils. By varying these thicknesses, the thickness of areas A and B can be varied by combining multiple layers with same or different thicknesses, densities, and sizes.

For an imaging body of a given density, a thicker imaging body will produce a brighter radiographic image than a thinner body. A thicker imaging body is more radiopaque and blocks more radiation than a thinner imaging body, so the body appears brighter in the resulting radiographic image. A thinner imaging body is more radiolucent and appears dimmer in the radiographic image. Thus, the thickness of the imaging body 203 may be varied to obtain the desired amount of radiolucence and/or radiopacity.

Preferably at least a portion of the imaging body 203 is partially radiolucent, or semiopaque, meaning that it only partially blocks radiation and allows some radiation to pass through. Radiolucent imaging markers are particularly desirable for imaging tissue because they do not completely obscure the tissue beneath the marker. A completely radiopaque marker blocks all radiation from passing through to the tissue below it. By contrast, a radiolucent marker allows some radiation to pass through and image the tissue below. The radiolucent marker appears as a faint or light gray color on the radiographic image, and the tissue below the marker is visible.

When the two imaging rings 220, 222 are placed together on the marker substrate 204, as shown by the dotted lines L in FIG. 2C, the overlapping area A is thicker than the non-overlapping area B and thus is less radiolucent. Area A has a higher radiographic density (as shown on a resulting radiographic image) than area B. The overlapping area A blocks more radiation than does the non-overlapping area B. An example of a radiographic image of a multi-density skin marker is shown in FIG. 2D. The outer portion of the outer ring 220 forms the non-overlapping area B and appears fainter in the image than the inner ring 222 which forms the overlapping area A. Both rings are radiolucent or semiopaque, allowing some radiation to pass through to image the tissue below.

The multi-density marker 200 with the overlapping imaging rings 220, 222 creates the two-toned or two-shaded image shown in FIG. 2D. When the imaging exam is used to image dense tissue, such as dense breast tissue, the overlapping area A is less likely than the non-overlapping area B to wash out or disappear from the image. As the image shows, the overlapping area A blocks more radiation than does the non-overlapping area B. Over time, during a long exposure to radiation, the non-overlapping area B may become fully penetrated by the radiation, such that it disappears entirely or almost entirely from the image. The overlapping area A will still appear on the image after the non-overlapping area B has disappeared. The multi-density image can be very useful for images of dense tissue, where longer exposure times provide a clearer image of the tissue. The overlapping area A will still be visible, identifying the location of the skin marker 200, after the non-overlapping area B has faded from view.

For example, the multi-density marker 200 is useful in MLO (mediolateral oblique) and RCC/LCC (right or left craniocaudal) breast exams. These are side to side and top to bottom mammography exams that are used to image breast tissue. The multi-density marker 200 appears more clearly in these images than single density markers, especially when the breast tissue being imaged is dense.

Varying thicknesses in the overlapping and non-overlapping areas of the imaging shapes give a third dimension to the resulting radiographic image, adding depth and providing a three-dimensional perspective. The different thicknesses appear in the image with different brightnesses, thereby clearly identifying the thickness dimension in the image. The additional perspective added by this multi-density marker can assist the radiologist or other medical caretaker in properly orienting the image and making an accurate diagnosis.

The multi-density skin marker of the present invention is not limited to overlapping imaging bodies. Overlapping imaging bodies, such as the overlapping rings 220, 222 described above, are one way to create a multi-density radiographic image, because the thicker, overlapping region is radiographically denser than the thinner non-overlapping region. But the multi-density radiographic image can also be created with a multi-density skin marker having two, non-overlapping imaging bodies. For example, in one embodiment, a multi-density skin marker 300 includes a first imaging body 320 and a second imaging body 322 positioned next to each other on a marker substrate 304. The two imaging bodies 320, 322 do not overlap. They can be positioned adjacent, near, or far from each other on the marker substrate 304. The first imaging body 320 has a thickness (and/or density) that is different from the thickness (and/or density) of the second imaging body 322. Due to this difference in thickness (and/or density), the first imaging body 320 has a different radiographic density and will reflect a different amount of radiation than the second imaging body 322, thereby creating a multi-density radiographic image with two or more different shades or tones.

In another embodiment of the invention, a multi-density skin marker 300' includes a multi-density imaging body 303' having a single imaging body 336. The imaging body 336 varies in thickness (and/or density) at some portion of the body. For example, the portion 336a on the right side of the imaging body can be thicker (and/or denser) than the portion 336b on the left side of the imaging body. The change in thickness (and/or density) can be gradual or abrupt. A specific area of the imaging body can be made thicker (and/or denser) than the remainder of the imaging body. Because the thicker (and/or denser) area has a different radiographic density than the thinner (and/or less dense) area, the marker 300' creates a multi-density radiographic image.

As the above description shows, the multi-density skin marker can utilize one or more imaging bodies with various thicknesses and/or densities. Different materials, thicknesses, and densities can be combined in the imaging body to create the desired multi-density skin marker and the resulting multi-density radiographic image. The imaging bodies may be made of any suitable radiopaque material, such as vinyl, rubber, plastic, foam, wire, paste, and ink.

Figure 4A:
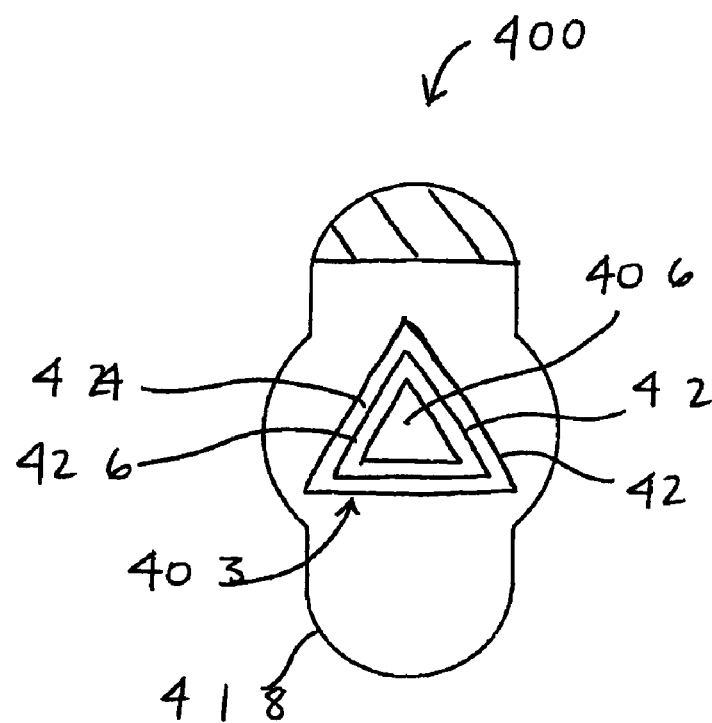
FIG. 4A is a rear view of a multi-density skin marker in an embodiment according to the invention.

Furthermore, the multi-density imaging marker can be shaped in many ways, other than the rings shown in FIGS. 2A-D and 3A-B. Another exemplary embodiment is shown in FIG. 4A, where the dual density imaging body 403 has a triangular shape. The imaging body 403 includes two imaging triangles 424, 426. The inner imaging triangle 426 overlaps the outer imaging triangle 424. The inner imaging triangle 426 has an outside perimeter 427 that is smaller than the outside perimeter 425 of the outer imaging triangle 424. The central opening 406 also has a triangular shape, although it is not limited to this shape. In another embodiment, the two triangles may be next to each other instead of overlapping, with one triangle having a different thickness and/or density than the other.

Figure 4B:
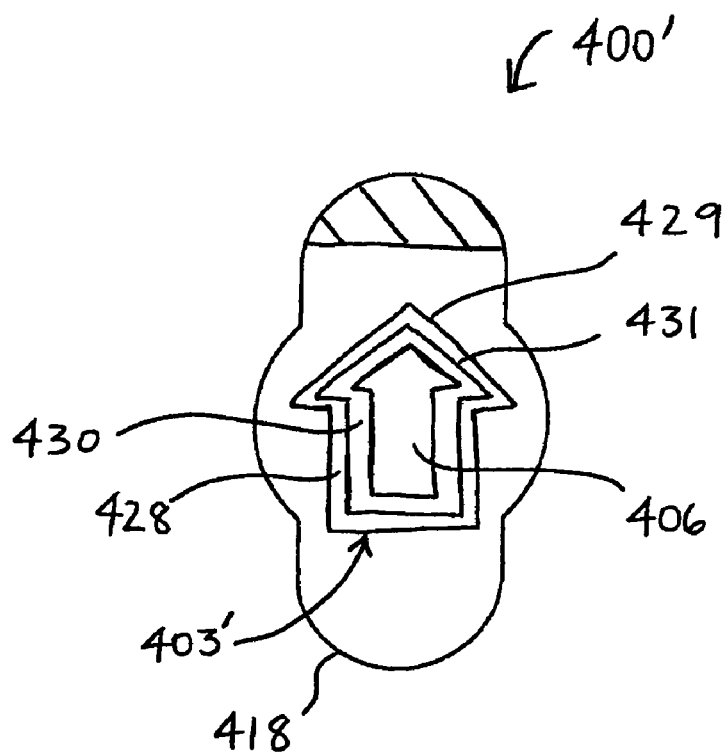
FIG. 4B is a rear view of a multi-density skin marker in an embodiment according to the invention.

Referring to FIG. 4B, a skin marker 400' according to another exemplary embodiment of the invention includes a dual density imaging body 403'. The imaging body 403' includes an inner imaging arrow 430 overlapping an outer imaging arrow 428. The inner imaging arrow 430 has an outside perimeter 431 that is smaller than the outside perimeter 429 of the outer imaging arrow 428. The central opening 406 in this embodiment also takes the shape of an arrow, although it could have any other suitable shape. The outer perimeter 418 of the marker may also vary in size, to create smaller or larger markers 400'. The embodiments shown here are just a few examples of the many shapes that the dual density imaging body may take, and are not meant to be limiting in any way.

Although the embodiments described above include two imaging shapes, more than two imaging shapes may be used to create a multi-layered marker. For example, three or more imaging rings or other shapes can be overlapped with each other to create multiple overlapping and non-overlapping areas of different radiographic densities. Three or more imaging bodies with varying thicknesses (and/or densities) can also be positioned on the skin marker with or without overlapping. The multi-layered marker can then create a multi-toned or multi-shaded radiographic image. Also, as described above, a single imaging body with a changing thickness (and/or density) can also be used to create the multi-toned radiographic image.

Figure 5:
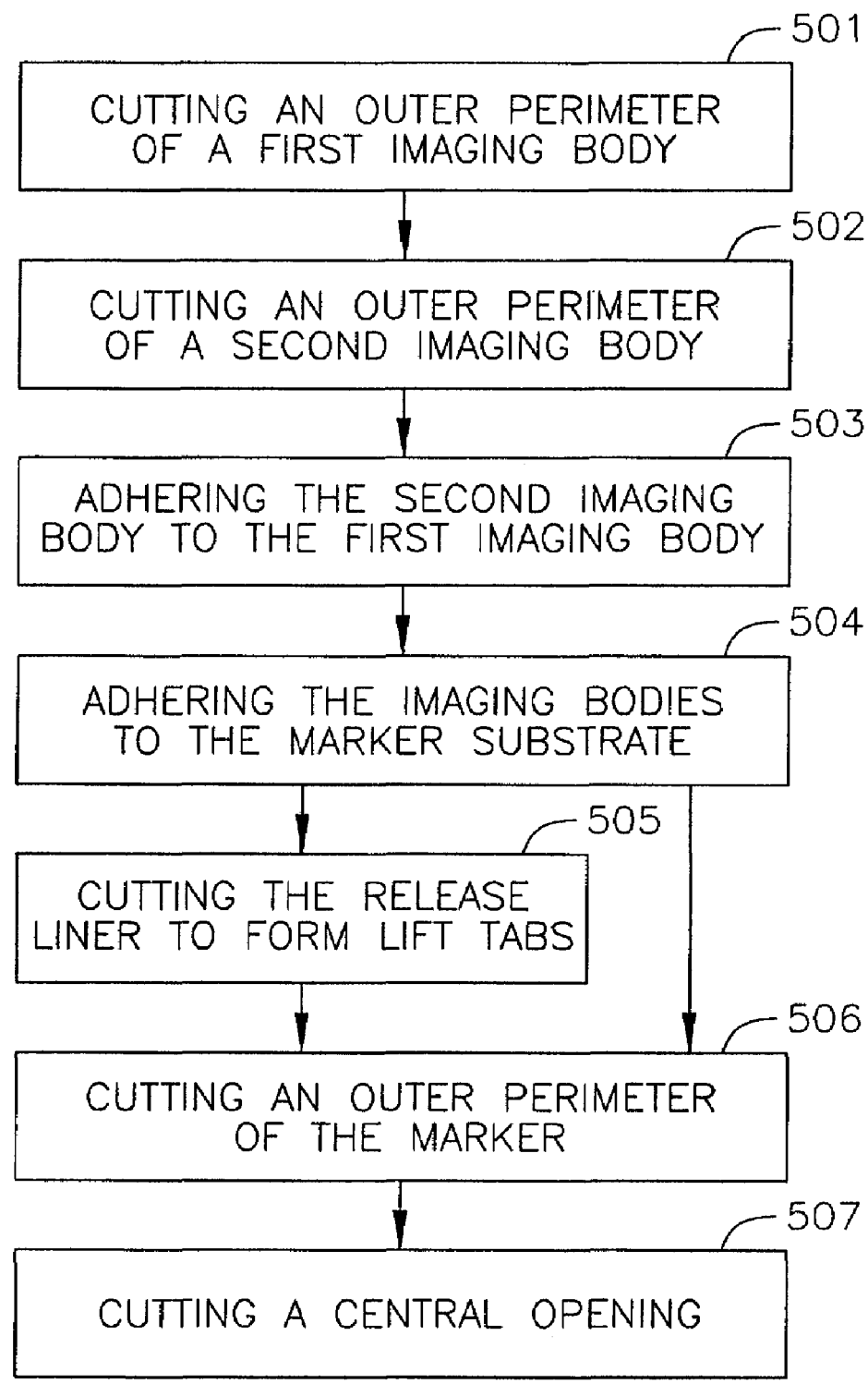
FIG. 5 is a flowchart of a method of manufacturing a multi-density skin marker according to an embodiment of the invention.

Referring to FIG. 5, in one embodiment of the invention, a method of manufacturing a multi-density skin marker includes cutting an outer perimeter of an imaging body. For purposes of describing the manufacturing method, the imaging bodies will be described as imaging rings. However, it will be understood that the imaging bodies may take any suitable shape, as discussed more fully above. The manufacturing process is also described with reference to two imaging bodies, but the process may be modified to include more or less than two imaging bodies, to create the multi-density markers described above.

The manufacturing method includes cutting the outer perimeter of one of the two imaging rings from a web, sheet, or roll of the imaging material 501. For example, this may include cutting the outside diameter D2 of the inner imaging ring 222 (shown in FIG. 2C). The imaging material may be a vinyl material with a medical grade adhesive coated on one side of the vinyl, and a release liner 640 (shown in FIG. 6) covering the adhesive. Once the outer diameter or perimeter of the first imaging body has been cut, the remaining vinyl surrounding that diameter or perimeter is stripped away from the release liner and discarded. The first imaging marker is left on the release liner 640.

The method then includes cutting the outer diameter or perimeter of a second imaging body 502. For example, a second web, sheet, or roll of vinyl material with an adhesive and release liner on one side may be used for the second imaging body. As an example, the shape that is cut may be the outside diameter D3 of the outer imaging ring 220. The release liner is stripped away from the vinyl material either before or after the outer shape of the second imaging body is cut. After the outer shape of the second imaging body has been cut, the remaining vinyl material surrounding the cut shape is also stripped away and discarded.

The method then includes adhering the second imaging body to the first imaging body 503. For example, the inner imaging ring 222 may be adhered directly to the adhesive side of the outer imaging ring 220. In an exemplary embodiment, the second imaging marker is adhered to the first marker at the same time that it is cut from the roll or sheet of vinyl material. The first imaging body, such as the inner imaging ring 222, can be adhered to the second sheet of vinyl material as the second sheet is being cut into the shape of the second imaging body 220. In this embodiment, the release liner for the second roll of vinyl material is stripped away before the second imaging shape is cut, exposing the adhesive underneath. The second imaging body is then cut into its perimeter shape as it is stamped onto and adhered to the first imaging body. The remaining vinyl material outside the perimeter is then discarded. The two imaging bodies are then adhered to each other on the release liner 640.

In one embodiment, the two imaging bodies are adhered together in the desired overlapping arrangement. For example, when the two imaging rings 220 and 222 shown in FIGS. 2A-C are manufactured, the two rings are adhered to each other such that the inner ring 222 is centered with respect to the outer ring 220, with the outer ring 220 overlapping the inner ring 222. Other arrangements are possible to create different overlapping or non-overlapping areas between the two imaging bodies.

With the two imaging bodies adhered together, the method then includes adhering the imaging bodies to the marker substrate 504. The marker substrate is provided in the form of a web, sheet, or roll of label stock, film, or any other suitable material for the marker substrate. One side of the substrate is at least partially covered with an adhesive, which may in turn be covered by a release liner. The release liner is stripped away and discarded to expose the adhesive. The two imaging bodies are then adhered or laminated to the adhesive side of the marker substrate.

The method then includes the optional step of cutting the release liner (640 in FIG. 6) to create lift tabs 505 in order to form the non-adhesive area 214 on the bottom surface 232 of the marker. Only the release liner is cut to form this non-adhesive area; the imaging bodies 222, 220 and the marker substrate 204 need not be cut.

The method then includes cutting the marker substrate material to form the desired outer perimeter of the final skin marker 506. For example, the outer perimeter 218 of the marker 200 (shown in FIG. 2B) may be cut. The remaining marker substrate material surrounding the cut shape is stripped away and discarded.

Finally, the method includes the optional step of cutting through all of the layers of the marker—in this embodiment, the release liner 640, both vinyl markers 220, 222, and the marker substrate 204—to form a central opening 507. For example, the circular central opening 206 (shown in FIGS. 2A-C) may be cut through the center of the marker. The material that is cut away to form this opening is stripped away and discarded, by air ejecting or otherwise discarding it. The finished skin markers on the release liner 640 can then be packaged as desired.

The method described above may be modified to vary the size, shape, thickness, and arrangement of the skin marker. For example, the method may be used to create a multi-density marker by cutting and adhering a third imaging body to the marker. The placement of the multiple imaging bodies can be adjusted to obtain the desired overlapping arrangement, or to obtain a non-overlapping arrangement. The order of the method is also not essential and may be varied as, for example, the outer perimeter of the marker may be cut before or after the lift tab is cut, or before or after the central opening is cut. The imaging bodies may be adhered to the top surface 234 of the marker substrate instead of the bottom surface 232. Other variations will be apparent to those skilled in the art.

Figure 6:
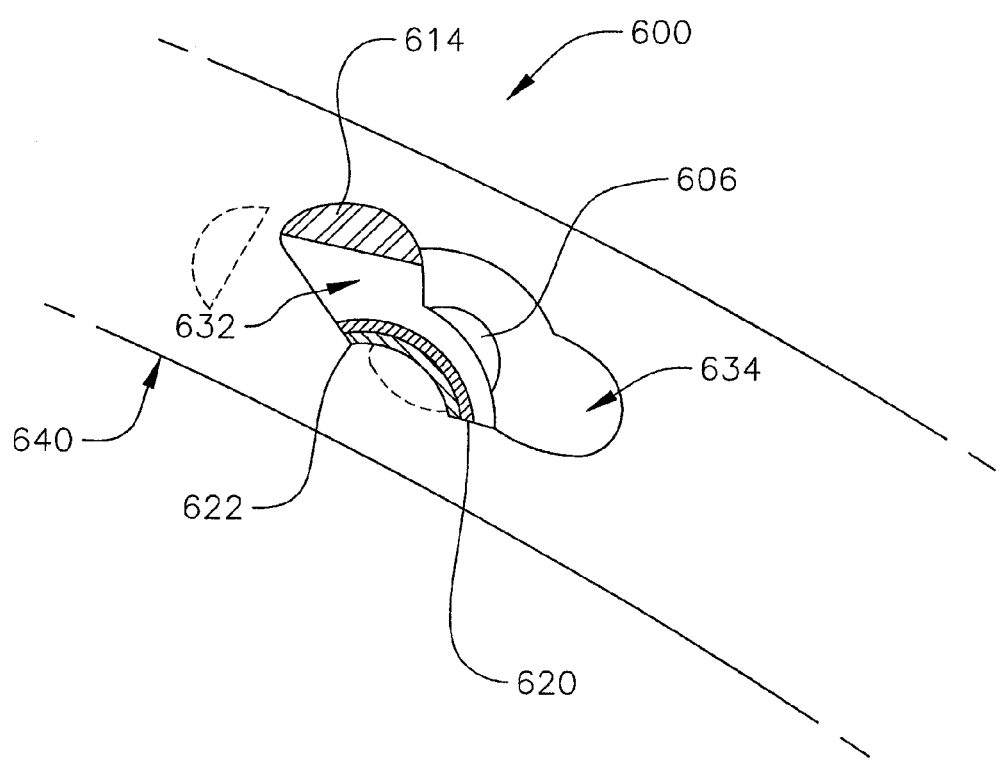
FIG. 6 is a perspective view of a multi-density skin marker according to an exemplary embodiment of the invention.

An exemplary embodiment of a skin marker 600 manufactured according to the method described above is shown in FIG. 6. The marker 600 rests on the release liner 640. The dotted lines show where the release liner 640 has been cut to form the central opening 606 and the lift tab 614. Either or both surfaces of the release liner 640 may be pre-printed with symbols, words, images, colors, or any other indications to provide information about the marker 600 and/or any other pertinent information. In FIG. 6, the marker 600 is shown folded upwards away from the release liner 640 to reveal the bottom surface 632 of the marker, with the lift tab 614, inner imaging ring 622, and outer imaging ring 620. As described above, the bottom surface 632 is at least partially covered with adhesive.

Figure 7:
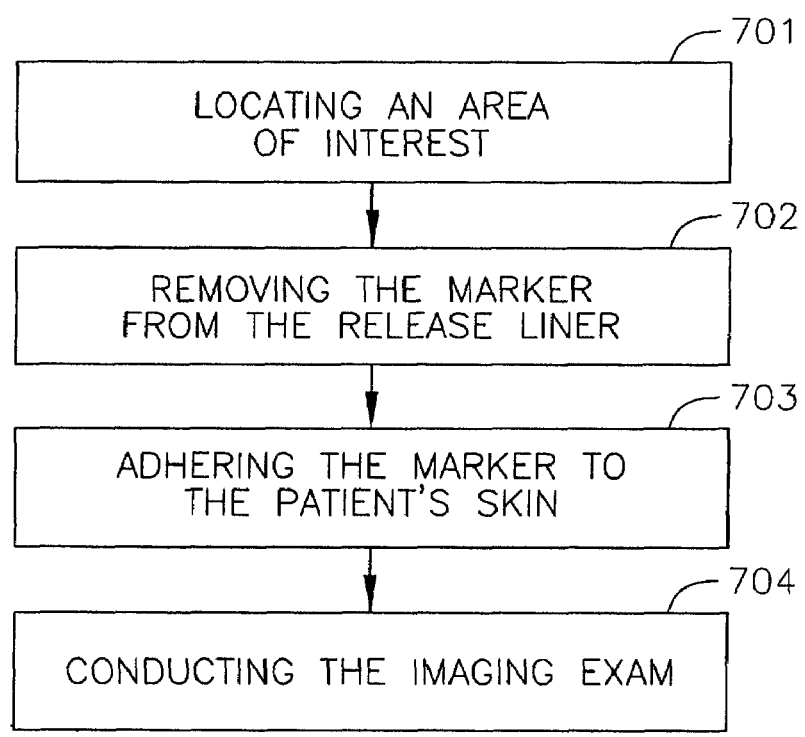
FIG. 7 is a flowchart of a method of using a multi-density skin marker according to an embodiment of the invention.

A method of using a multi-density skin marker for a radiographic imaging exam of a patient according to an exemplary embodiment of the invention is shown in FIG. 7. The method includes locating an area of interest on or near the patient's skin 701. The method also includes peeling or removing the marker away from the release liner 702. Removing the marker from the release liner exposes the adhesive on the bottom surface of the marker. If a portion of the release liner has been cut to form lift tabs, that portion of the release liner remains adhered to the marker to form the non-adhesive area for the lift tab. The method then includes adhering the marker to the patient's skin 703 on or near the area of interest. The bottom surface of the marker directly contacts the patient's skin. The method then includes conducting the radiographic imaging exam of the patient 704, with the marker in place. The exam may be a mammography. After the exam, the marker can be repositioned on the patient if necessary for another exam, or it can be simply removed and discarded.

Although limited embodiments of a multi-density skin marker have been specifically described and illustrated herein, many modifications and variations will be apparent to those skilled in the art. Accordingly, it is to be understood that the multi-density skin marker constructed according to principles of this invention may be embodied other than as specifically described herein. The invention is also defined in the following claims.

What is claimed is:

1. A multi-density skin marker comprising:
    a marker substrate; and
    a multi-density imaging body attached to a surface of the marker substrate,
    wherein the marker substrate is distinct from the multi-density imaging body,
    wherein the multi-density imaging body comprises a first imaging body attached to the marker substrate and a second imaging body attached to one of the first imaging body or the marker substrate such that the multi-density imaging body comprises first and second radiographic densities, and wherein the first radiographic density differs from the second radiographic density such that a radiographic image of the multi-density skin marker comprises a plurality of shades, and
    wherein both the first and second radiographic densities are discernible in such image.

2. The multi-density skin marker of claim 1, wherein the first imaging body comprises a first imaging shape an the second imaging body comprises a second imaging shape at least partially overlapping the first imaging shape.

3. The multi-density skin marker of claim 2, wherein the first imaging shape is a first ring having a first outer diameter and the second imaging shape is a second ring having a second outer diameter, and wherein the first outer diameter differs from the second outer diameter.

4. The multi-density skin marker of claim 3, wherein the first outer diameter is larger than the second outer diameter and wherein the second ring is adhered to the first ring whereby the second ring overlaps the first ring.

5. The multi-density skin marker of claim 2, wherein the first imaging shape is a first triangle having a first outer perimeter and the second imaging shape is a second triangle having a second outer perimeter.

6. The multi-density skin marker of claim 2, wherein the first and second imaging shapes are arrows.

7. The multi-density skin marker of claim 1, wherein the first imaging body has a first thickness and the second imaging body has a second thickness that differs from the first thickness.

8. The multi-density skin marker of claim 1, wherein the first imaging body has a first radiographic density and the second imaging body has a second radiographic density that differs from the first density.

9. The multi-density skin marker of claim 1, wherein the marker substrate comprises an adhesive surface.

10. The multi-density skin marker of claim 9, wherein the multi-density imaging body is adhered to the adhesive surface of the marker substrate.

11. The multi-density skin marker of claim 9, wherein the adhesive surface of the marker substrate is configured to touch a patient's skin.

12. The multi-density skin marker of claim 9, wherein the adhesive surface of the marker substrate comprises a non-adhesive area at an end of the marker substrate.

13. The multi-density skin marker of claim 1, wherein the multi-density imaging body surrounds a central opening in the marker substrate.

14. The multi-density skin marker of claim 1, wherein the first and second imaging bodies are each constructed from a material selected from the group consisting of vinyl, rubber, plastic, foam, wire, and ink.

15. The multi-density skin marker of claim 1, wherein the second imaging body is attached to the marker substrate.

16. The multi-density skin marker of claim 15, wherein the first and second imaging bodies are contacting each other and attached side-by-side to the marker substrate, the first and second imaging bodies each having a different radiographic density.

17. The multi-density skin marker of claim 1, wherein the second imaging body is attached to the first imaging body.

18. The multi-density skin marker of claim 17, wherein the first imaging body comprises a first ring of semiopaque material adhered to an adhesive bottom surface of the marker substrate, and the second imaging body comprises a second ring of semiopaque material adhered to the first ring and at least partially overlapping the first ring.

19. The multi-density skin marker of claim 1, wherein the first and second imaging bodies cover less than an entire area of the marker substrate.

20. A multi-density skin marker comprising:
    a marker substrate having an adhesive surface; and
    a multi-density imaging body comprising a first imaging shape adhered to the marker substrate and a distinct second imaging shape adhered to and at least partially overlapping the first imaging shape, such that the multi-density imaging body has at least a first and a second different radiographic densities that are each discernible in a radiographic image, and wherein the marker substrate is distinct from the multi-density imaging body.

21. The multi-density skin marker of claim 20, wherein the multi-density imaging body is adhered to the adhesive surface of the marker substrate.

22. The multi-density skin marker of claim 21, wherein the first imaging shape comprises a first ring having a first outer diameter and the second imaging shape comprises a second ring having a second outer diameter that is different than the first outer diameter.

23. A method of creating a multi-density radiographic image, comprising:
   providing a multi-density skin marker comprising a marker substrate with an adhesive surface for contacting a person's skin, a first imaging body attached to the marker substrate, and a second imaging body attached to one of the first imaging body or the marker substrate such that the skin marker has a first portion with a first radiographic density and a second portion with a second radiographic density, and wherein the marker substrate is distinct from the first and second imaging bodies; and
   creating an image of the first portion having a first shade and of the second portion having a second shade different from the first shade.

24. The method of claim 23 wherein the first radiographic density is greater than the second radiographic density and the first shade is brighter than the second shade.

25. A method of manufacturing a multi-density skin marker, comprising:
   cutting a first outer perimeter of a first imaging body from a first semiopaque material;
   cutting a second outer perimeter of a second imaging body from a second semiopaque material;
   adhering the first and second imaging bodies to each other in an overlapping relationship; and
   adhering the first and second imaging bodies to a marker substrate that is distinct from the two imaging bodies.

26. The method of claim 25, further comprising cutting a central opening through the first imaging body, the second imaging body, and the marker substrate.

27. The method of claim 25, wherein the method further comprises adhering the marker substrate to a release liner and cutting the release liner to form at least one lift tab at an end of the multi-density skin marker.

28. The method of claim 25, further comprising adhering the first and second imaging bodies to an adhesive bottom surface of the marker substrate.

* * * * *